US009687317B2

(12) United States Patent
Getto et al.

(10) Patent No.: US 9,687,317 B2
(45) Date of Patent: Jun. 27, 2017

(54) ORTHODONTIC TREATMENT PLANNING USING VIRTUAL ARTICULATOR

(71) Applicant: OraMetrix, Inc., Richardson, TX (US)

(72) Inventors: Phillip Getto, Plano, TX (US); Peer Sporbert, Berlin (DE); Markus Kaufmann, Berlin (DE)

(73) Assignee: OraMetrix, Inc., Richardson, TX (US)

( * ) Notice: Subject to any disclaimer, the term of this patent is extended or adjusted under 35 U.S.C. 154(b) by 720 days.

(21) Appl. No.: 14/144,726

(22) Filed: Dec. 31, 2013

(65) Prior Publication Data

US 2014/0188448 A1  Jul. 3, 2014

Related U.S. Application Data

(60) Provisional application No. 61/748,069, filed on Dec. 31, 2012.

(51) Int. Cl.
| | |
|---|---|
| *G06G 7/48* | (2006.01) |
| *A61C 7/00* | (2006.01) |
| *A61B 6/14* | (2006.01) |
| *G06F 19/00* | (2011.01) |
| *A61B 6/03* | (2006.01) |
| *A61B 6/00* | (2006.01) |
| *A61C 11/00* | (2006.01) |

(52) U.S. Cl.
CPC ............ *A61C 7/002* (2013.01); *A61B 6/14* (2013.01); *G06F 19/3437* (2013.01); *A61B 6/032* (2013.01); *A61B 6/4085* (2013.01); *A61C 11/00* (2013.01)

(58) Field of Classification Search
CPC ..... A61C 7/002; A61C 11/00; G06F 19/3437; A61B 6/14; A61B 6/4085; A61B 6/032
USPC ............................................................ 703/6
See application file for complete search history.

(56) References Cited

U.S. PATENT DOCUMENTS

2009/0191503 A1*  7/2009  Matov ...................... A61C 7/00
                                                                 433/24

* cited by examiner

*Primary Examiner* — Saif Alhija
(74) *Attorney, Agent, or Firm* — McDonnell Boehnen Hulbert & Berghoff LLP

(57) ABSTRACT

The present invention discloses orthodontic treatment planning using virtual articulator with the help of a computer workstation. A virtual articulator can be activated from the workstation. The virtual articulator displays opening/closing movements, and left/right excursive movements. One can also adjust the angle of the articular eminence to more accurately display the patient's chewing motion. Treatment planning simulation using virtual articulator can detect collision of teeth and lead to a treatment plan that can avoid such collisions. Composite three dimensional models of dentition obtained by scanning of teeth and through CBCT are used in identifying the articulator; which is then used in virtual simulation by means of software instructions in the workstation.

5 Claims, 5 Drawing Sheets

__US 9,687,317 B2__

ORTHODONTIC TREATMENT PLANNING USING VIRTUAL ARTICULATOR

CROSS-REFERENCE TO RELATED APPLICATIONS

This application is a non-provisional application of the provisional application, Ser. No. 61/748,069, filed Dec. 31, 2012. Priority of the filing date of the provisional application is hereby claimed for the instant application. The subject matter of this application is related to the subject matter of the following applications. Priority to the related applications is not claimed under 35 U.S.C. §120.

Application Ser. No. 13/107,913, filed May 15, 2011, pending; provisional application Ser. No. 61/642,646, filed May 4, 2012; and non-provisional application Ser. No. 13/887,323.

The entire contents of each of the above listed patent applications are incorporated by reference herein.

BACKGROUND OF THE INVENTION

A. Field of the Invention

This invention relates generally to the field of orthodontics. More particularly, the invention relates to planning orthodontic treatment for a patient using virtual articulator.

B. Description of Related Art

There are numerous patents issued in the area of orthodontic treatment planning to cure mal-occlusion of a patient. However, they lack in the area of consideration of the behavior of the articulator in planning the treatment.

The present invention meets this need.

SUMMARY OF THE INVENTION

The present invention discloses orthodontic treatment planning using virtual articulator on a computer workstation.

The virtual articulator is activated from the workstation. The virtual articulator displays opening/closing movements, and left/right excursive movements. The angle of the articular eminence is adjusted to more accurately display the patient's chewing motion. Treatment planning simulation using virtual articulator facilitates detection of collision between teeth thereby helping in devising a treatment plan that can avoid such collisions. Other undesirable teeth positioning can be avoided as well.

Composite three dimensional models of dentition obtained by scanning of teeth and through CBCT are used in identifying the articulator; which is then used in virtual simulation by means of software instructions in the workstation.

BRIEF DESCRIPTION OF THE DRAWINGS

Presently preferred embodiments of the invention are described below in reference to the appended drawings, wherein like reference numerals refer to like elements in the various views, and in which.

DETAILED DESCRIPTION OF PREFERRED EMBODIMENT

The virtual articulator can be activated in the workstation. The virtual articulator displays opening/closing movements, and left/right excursive movements of the jaws. One can also adjust the angle of the articular eminence to more accurately display the patient's chewing motion.

Figure 1:
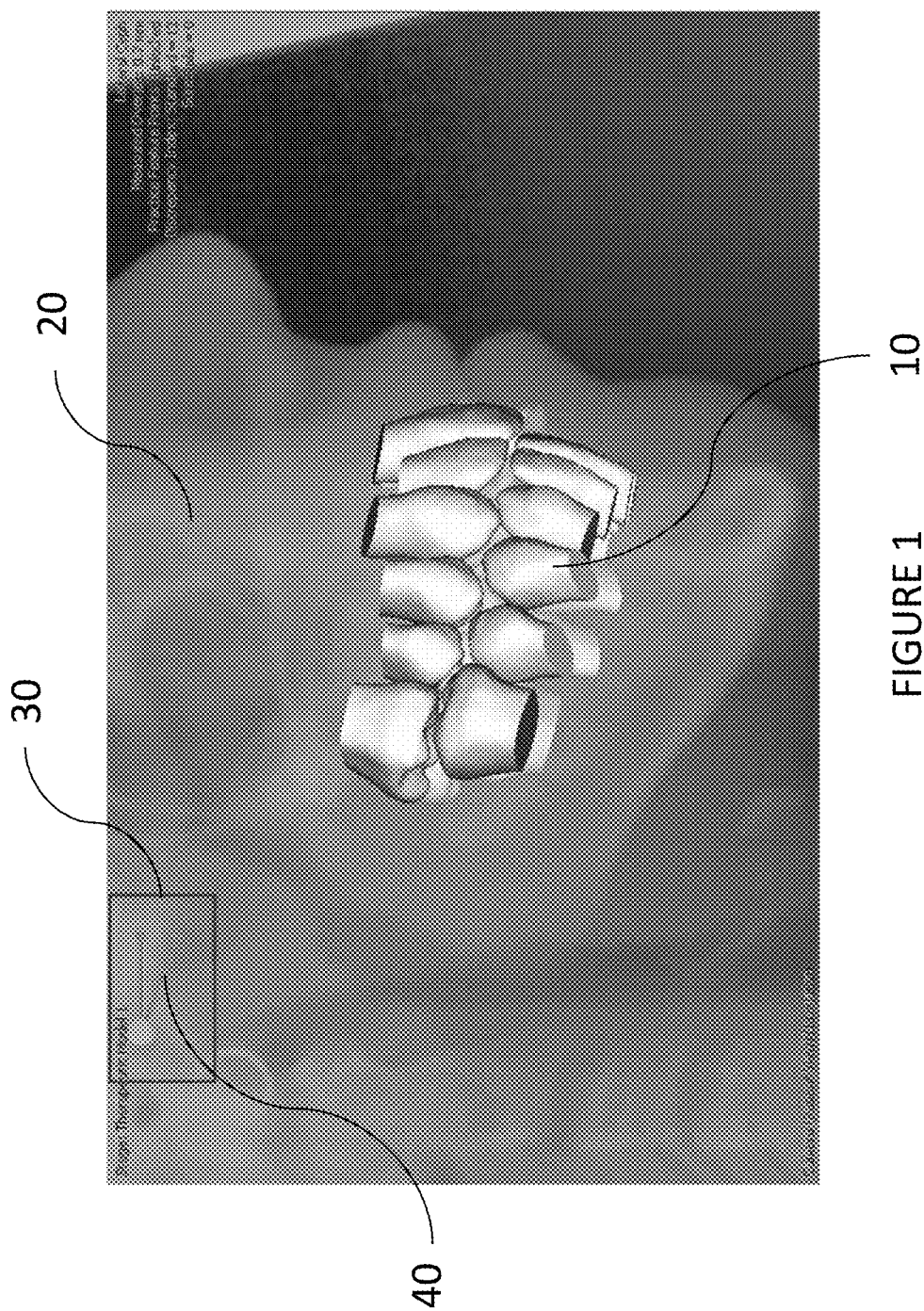
FIG. 1 shows the virtual 3-D model of the teeth of a patient combined with CBCT model of the bone structure including the articulator.

FIG. 1 shows the virtual 3-D model 10 of the teeth of a patient integrated with CBCT model 20 of the bone structure including the articulator portion 30 with articular eminence slope line 40. The 3-D model of the teeth is obtained through scanning of the teeth. The scanning can be done in-vivo or of a physical model, such as a plaster model created from impression, of the teeth.

Figure 2:
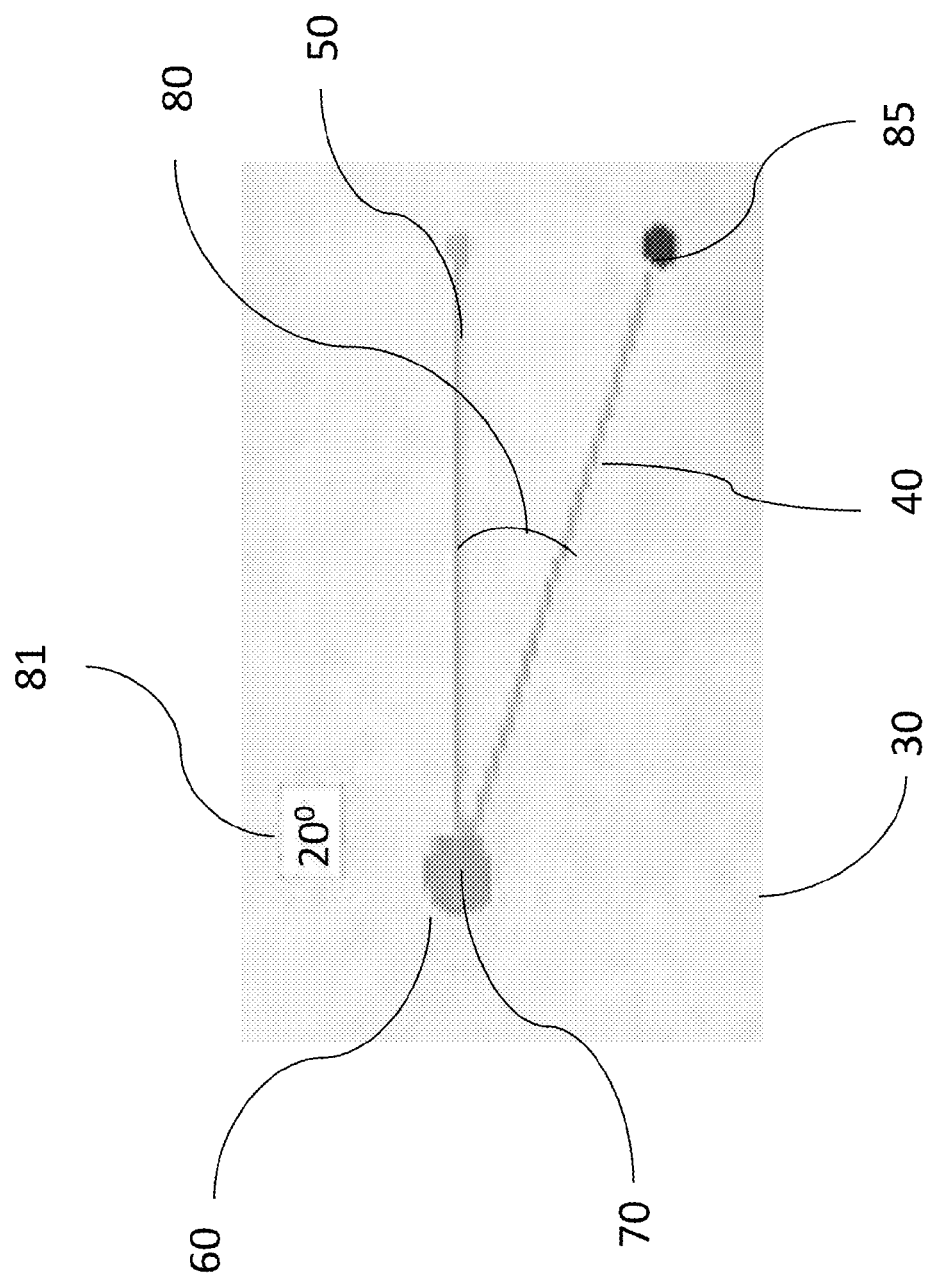
FIG. 2 show the articulator from FIG. 1 in more detail.

FIG. 2 show an enlarged view of the articulator portion 30 from FIG. 1 in more detail. FIG. 2 shows articular eminence slope line 40, Frankfort plane 50, dorsal point of articular eminence 70, condyle 60 and angle 80 between Frankfort plane 50 and articular eminence slope line 40. The value of the angle 80 in degrees is displayed in box 81. In FIG. 2, the angle 80 is set at the default value of 20°. Point 85 represents handle for changing the slope of articular eminence. The handle 85 is dragged up or down in order to define the slope of articular eminence relative to the horizontal (Frankfort) plane. The handle 85 is dragged anteriorly or posteriorly to shorten or lengthen the line. The angular value (in degrees) changes as the handle is moved. The slope of the articular eminence determines how the mandible slides forward and moves excursively as it opens. The length of the line of articular eminence determines how wide the bite will open in the chewing simulation. The condyle moves along the line of articular eminence when an articulation animation is carried out.

To begin with, the workstation provides software instructions with command controls in order to define the angle of the articular eminence during treatment planning.

Initially, the articular eminence slope line is shown by default in the cephalogram view, as this is the recommended view for setting the articular eminence slope.

Figure 3:
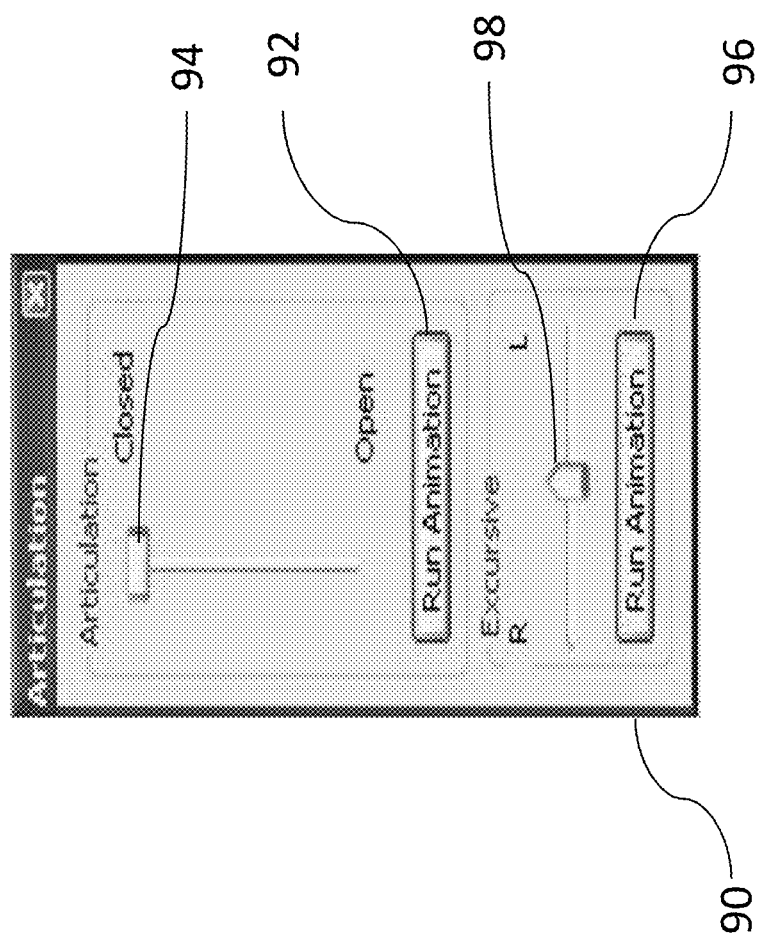
FIG. 3 shows the control box in the workstation for simulating the movement of the articulator and its impact on the teeth of the patient.

FIG. 3 shows an enlarged view of the control box 90 in the workstation for simulating the movement of the articulator and its impact on the teeth of the patient. Selection of control 92 enables the user in automatically performing the articulation simulation. On the other hand, the user can manually perform the animation by dragging the control 94 up or down. Selection of control 96 enables the user in automatically performing the excursive simulation. Here also, the user can manually perform the animation by dragging the control 98 left or right. Although not shown in FIG. 3, the jaws open and close during the articulation simulation and move side-ways during the excursive simulation and the condyle moves along the line of articular eminence.

Although not shown in FIG. 3, the user can view the upper and lower 3D teeth models occlusally with contacts.

Figure 4:
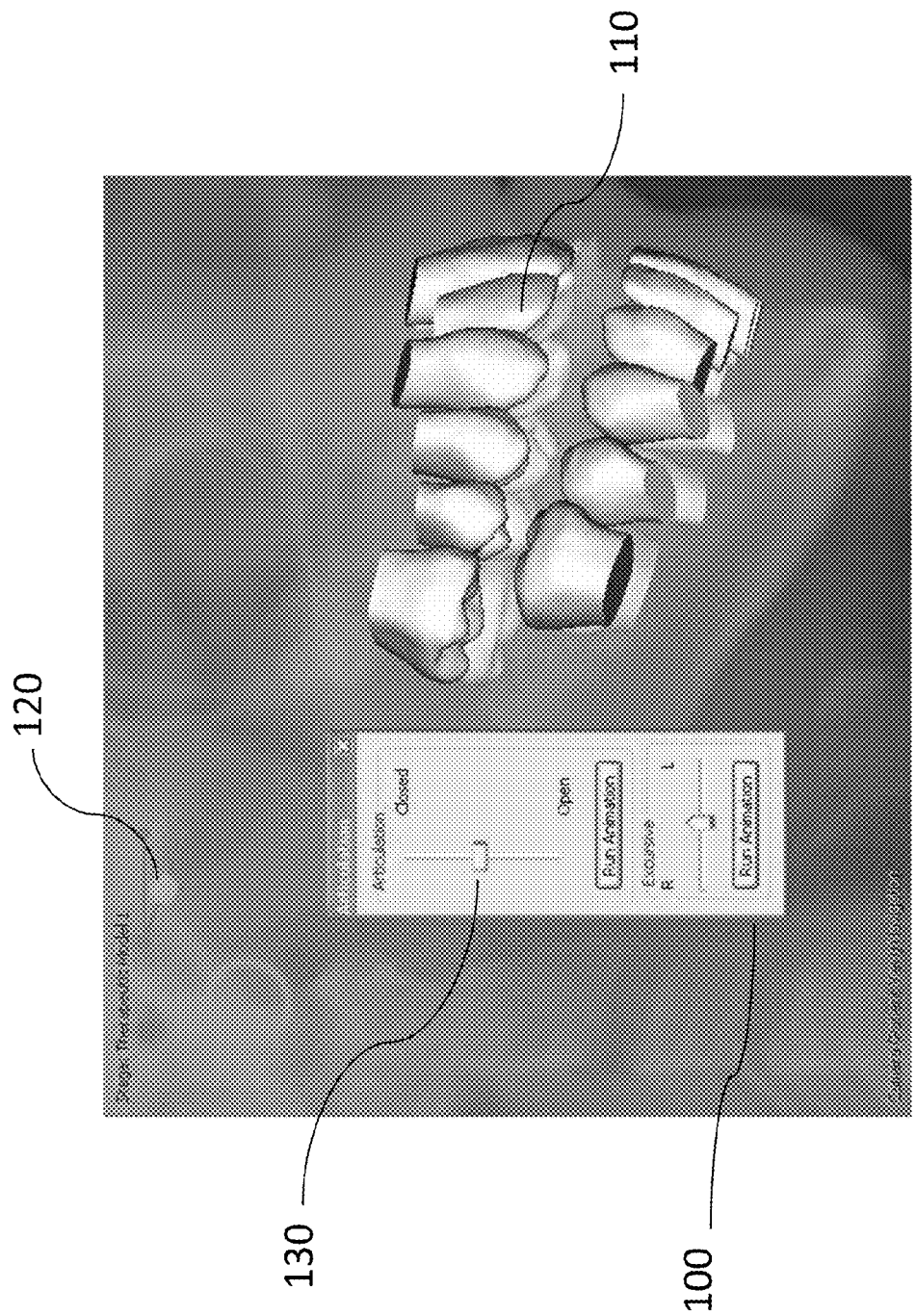
FIG. 4 shows an illustration of the virtual articulation simulation.

FIG. 4 shows an illustration of the virtual articulation simulation. FIG. 4 shows the teeth 110 in open position compared to the teeth 10 in FIG. 1. Also condyle 120 is moved to a different location compared to condyle 60 in FIG. 2 (and FIG. 1). FIG. 4 also shows control box 100 superimposed on the CBCT model. Control box 100 shows the articulation control 130 at the position, different from the position in FIG. 3, which caused the teeth to be in the open position 110. Although not shown in FIG. 4, in the side windows, user can check for any collisions.

Figure 5:
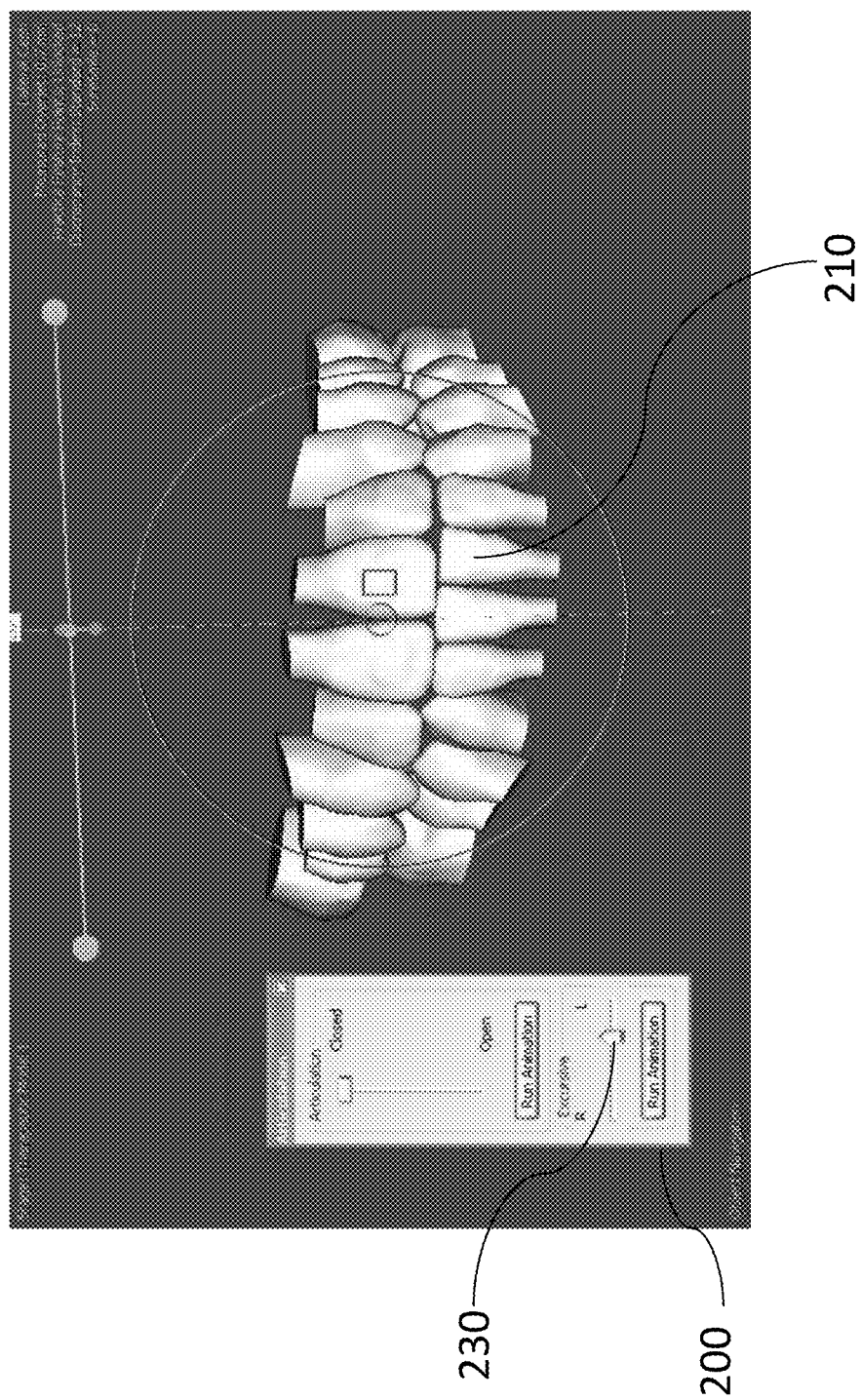
FIG. 5 shows an illustration of the virtual excursive simulation.

FIG. 5 shows an illustration of the virtual excursive simulation. FIG. 5 shows the teeth 210 in closed position compared to the teeth 10 in FIG. 1. FIG. 5 also shows control box 200 superimposed on the CBCT model. Control box 200 shows the excursive control 230 at the position, different from the position in FIG. 3, which caused the teeth to be in the closed position 210. The left-to-right movement (lateral excursion) is animated. Because the virtual articulator does not consider cuspid rise, multiple tooth collisions will be seen.

Although not shown in FIG. 5, the user checks for any tooth-collisions in the side windows in the workstation.

The process can be summarized as follows:
a. Obtain 3-D model of the teeth of a patient. Such a model can be derived from the digital image data obtained by scanning the teeth of the patient. Scanning may be performed in-vivo using a white light scanner or a laser scanner or any other suitable scanning device or on a physical model of the teeth obtained from impression.
b. Obtain a CBCT model of the facial bone structure, including virtual articulator, of the patient.
c. Integrate the 3-D teeth model and the CBCT model of the patient.
d. Perform virtual articulation simulation, and observe opening/closing movements of the patient's teeth and jaws.
e. Perform virtual excursive simulation, and observe left/right excursive movements of the patient's teeth and jaws.
f. Check for any teeth collisions and other mal-functions in the patient's dentition.
g. Modify treatment plan in order to avoid tooth-collisions.
h. Modify treatment plan in order to remove any other mal-functions.
i. Adjust the angle of the articular eminence to more accurately display the patient's chewing motion; and repeat Steps d-h.

In summary, the present invention discloses orthodontic treatment planning using virtual articulator with the help of a computer workstation.

A virtual articulator can be activated from the workstation. The virtual articulator displays opening/closing movements, and left/right excursive movements. One can also adjust the angle of the articular eminence to more accurately display the patient's chewing motion. Treatment planning simulation using virtual articulator can detect collision of teeth and lead to a treatment plan that can avoid such collisions.

Composite three dimensional models of dentition obtained by scanning of teeth and through CBCT are used in identifying the articulator; which is then used in virtual simulation by means of software instructions in the workstation.

Presently preferred and alternative embodiments of the invention have been set forth. Variation from the preferred and alternative embodiments may be made without departure from the scope and spirit of this invention.

We claim:

1. A method of revising orthodontic treatment plan for a patient on a computer workstation using virtual articulator, comprising the steps of:
    a. obtaining a 3-D model of teeth of said patient;
    b. obtaining a CBCT model of facial bone structure, including virtual articulator, of said patient;
    c. integrating said 3-D teeth model and said CBCT model of said patient;
    d. performing virtual articulation simulation, and observing opening/closing movements of said patient's teeth and jaws;
    e. performing virtual excursive simulation, and observing left/right excursive movements of said patient's teeth and jaws;
    f. checking for any teeth collisions in said patient's dentition; and
    g. revising said treatment plan for said patient in order to avoid tooth-collisions if one or more are detected.

2. The method of claim 1, further comprising the step h. of adjusting angle of articular eminence to more accurately display said patient's chewing motion; and repeating Steps d-g.

3. The method of claim 1, further comprising the step of checking for other mal-functions in said patient's dentition; and revising said treatment plan for said patient in order to avoid other mal-functions if one or more are detected.

4. The method of claim 1, wherein said 3-D model of teeth of said patient is derived from digital data obtained by in-vivo scanning of said teeth of said patient.

5. The method of claim 1, wherein said 3-D model of teeth of said patient is derived from digital data obtained by scanning a physical model of said teeth of said patient.

* * * * *